United States Patent [19]

Muranishi et al.

[11] Patent Number: 4,994,281
[45] Date of Patent: Feb. 19, 1991

[54] POLYLACTIC ACID MICROSPHERES AND PROCESS FOR PRODUCING THE SAME

[75] Inventors: Shozo Muranishi; Yoshito Ikada; Hiroshi Yoshikawa; Shokyu Gen, all of Kyoto, Japan

[73] Assignees: Sanraku Incorporated, Tokyo; Biomaterials Universe Incorporated, Kyoto, both of Japan

[21] Appl. No.: 119,361

[22] Filed: Nov. 10, 1987

[30] Foreign Application Priority Data

Nov. 12, 1986 [JP] Japan .................................. 61-267507

[51] Int. Cl.$^5$ .............................................. H61K 9/16
[52] U.S. Cl. ..................................... 424/497; 424/426
[58] Field of Search ................................ 424/426, 497

[56] References Cited

U.S. PATENT DOCUMENTS

| 4,166,800 | 9/1979 | Fong | 424/497 X |
| 4,384,975 | 5/1983 | Fong | 424/497 X |
| 4,479,911 | 10/1984 | Fong | 424/497 X |
| 4,536,387 | 8/1985 | Sakamoto et al. | 424/426 |

Primary Examiner—Ferris H. Lander
Attorney, Agent, or Firm—Jordan and Hamburg

[57] ABSTRACT

Polylactic acid microspheres having an average particle diameter of about 0.1 to 10 μm which are produced from solution containing a physiologically active substance by the solvent-evaporation drying process. The microspheres are produced by emulsifying the solution in a non-solvent by the aid of ultrasonic wave. The microspheres produce a sustained release effect of the physiologically active substance.

5 Claims, 2 Drawing Sheets

Concentration of ACR in polylactic acid: (▲) 3%, (○) 5%, (■) 10%

Concentration of ACR in polylactic acid: (▲) 3%, (○) 5%, (■) 10%

(○) M̄w 3,400 (17.6μg-ADR/mg-sphere)

(●) M̄w 6,100 (10.2μg-ADR/mg-sphere)

(△) M̄w 13,000 (7.1μg-ADR/mg-sphere)

POLYLACTIC ACID MICROSPHERES AND PROCESS FOR PRODUCING THE SAME

BACKGROUND OF THE INVENTION

1. Field of the Invention:

The present invention relates to polylactic acid microspheres containing a physiologically active substance and a process for producing the same. 2. Description of the Prior Art:

The development of new pharmaceutical preparations based on the drug delivery system is being studied actively through the medical engineering approach and biopharmaceutic approach. The results of the development include new dosage forms prepared by utilizing polymeric thin membrane, deformed solid surface, liposome, emulsion, etc. Among them the one based on biodegradable polylactic acid is attracting attention.

Polylactic acid can be used as the polymer matrix for microspheres or as the coating substance for microcapsules. Microspheres are produced by the so-called solvent-evaporation drying process. According to this process, the polymer and drug are dissolved in a common solvent, a phase-separating the agent is added to the solution for emulsification, the solvent is distilled away, and residual fine particles are collected. (Refer to Chem. Pharm. Bull. 30, 2621–2628 (1982) and Japanese Patent Laid-open No. 33414/1980.) On the other hand, microcapsules are produced by the so-called phase-separation process which involves the steps of dispersing a physiologically active substance in a polylactic acid solution in which the substance is insoluble, adding a non-solvent for the polymer to bring about coacervation, and curing the polymer by a proper means. (Refer to Japanese Patent Laid-open No. 48923/1985.) According to the other known process, microencapsulation is accomplished by the in-water drying of three-layer emulsion.

The above-mentioned prior arts provide a drug delivery system which produces a certain effect but suffer from the limitations that they are not able to prepare microspheres having a diameter as small as several microns and they involve complicated processes. With this in mind, the present inventors studied the process for producing fine microspheres for sustained release preparation in a simple manner by the solvent-evaporation drying process. As a result, it was found that it is possible to produce microspheres having a diameter of several microns if the solution is treated with ultrasonic wave during emulsification. This finding led to the present invention.

SUMMARY OF THE INVENTION

Accordingly, it is an object of the present invention to provide polylactic acid microspheres having an average particle diameter of about 0.1 to 10μm which are produced from a solution containing a physiologically active substance by the solvent-evaporation drying process.

DETAILED DESCRIPTION OF THE INVENTION

Figure 1:
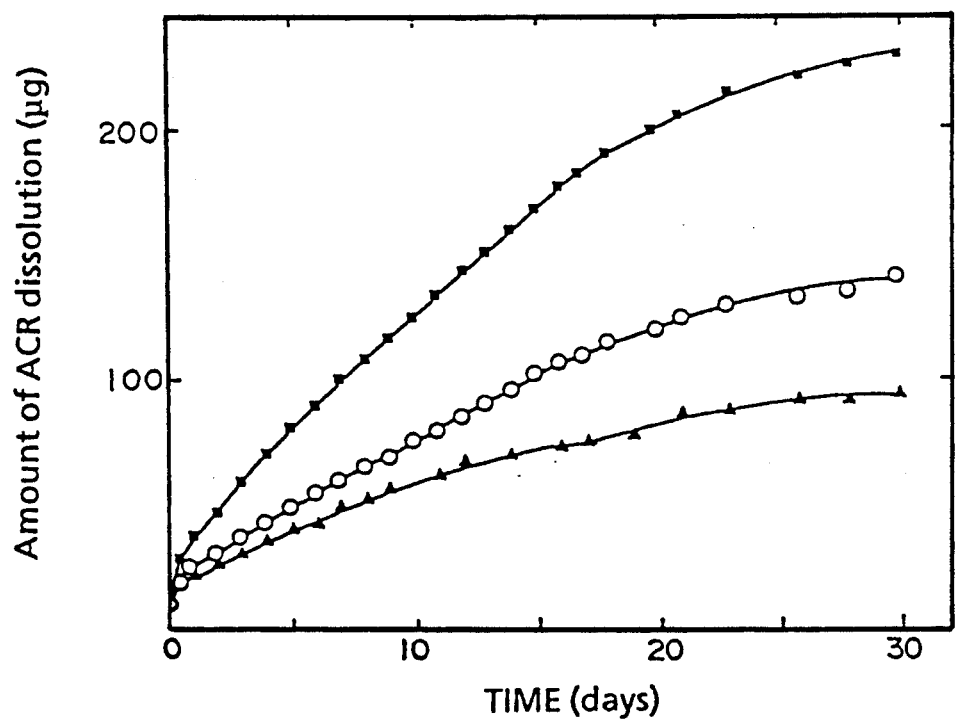
FIG. 1 is a graph showing the dissolution of ACR from three kinds of microspheres which differ in the initial ACR content.

The term "physiologically active substance" as used herein denotes any highly lipophilic drug having a high oil-water distribution ratio; and it also comprehends any drug soluble in both oil and water so long as it achieves the object of the invention.

Examples of such drugs include lipophilic anticancer drugs, antibiotics, antipyretics, analgesics, antiphlogistics, antitussives, sedatives, antiepileptics, antihistaminics, hypotensive diuretics, and diabetes remedies.

Examples of the anticancer drugs include aclarubicin, doxorubicin, pilarubicin, daynorubicin, bleomycin, actionmycin D, fluorouracil, tetrahydrofuryl-5-fluorouracil, and cisplatin.

Examples of the antibiotics include josamycin, kitasamycin, spiramycin, talamipicilin, chloramphernicol, rifampicin, and analogues thereof. Examples of the antipyretics, analgesics, and antiphlogistics include aspirin, etherenzamide, phenacetin, antipyrine, aminopyrine, indometacin, and phenylbutazone. Examples of the antitussives include papaverine hydrochloride and noscapine hydrochloride. Examples of the sedatives include chloropromazine hydrochloride, haloperidol, trifluoperazine, and chloradiazepoxide. Examples of the antiepleptics include diazepam, phenobarbital, and carbmazepine. Examples of the antihistaminics include promethazine hydrochloride, cyproheptadine hydrochloride, and diphenhydramine hydrochloride. Examples of the hypotensive diuretics include reserpine and spironolactone. Examples of the diabetes remedies include tolbutamide.

The content of the above-mentioned physiologically active substance varies depending on the kind of drug, desired pharmacological effect, and sustained release time. Thus it is not critical.

The microspheres having improved sustained release may range in particle diameter from several nanometers to hundreds of micrometers. Those of 0.1 to 10μm in particle diameter are preferable in consideration of the capability of intravenous injection, the directionality toward lymph, and the accumulation in reticuloendothelial systems such as liver and pancreas.

The polylactic acid used for microspheres is not limited in molecular weight; however, an oligomer of polylactic acid having a molecular weight lower than 10,000, preferably about 3,000 to 7,500, should be used where the rapid dissolution and decomposition of the drug in a living body are desirable.

With the polylactic acid microspheres of the present invention, it is possible to control the sustained release of physiologically active substances. In addition, taking advantage of their being uniform, extremely fine particles, it is also possible to cause an anticancer drug or the like to accumulate in lymph. These subjects will be discussed later.

The microspheres of the present invention can be produced by the following process, which is the second object of the invention. The process of the invention involves the steps of dissolving the above-mentioned physiologically active substance and polylactic acid in a solvent, emulsifying the solution in a non-solvent, while treating the solution with ultrasonic wave, thereby forming an o/w or o/o emulsion of fine particles, and distilling away the first solvent.

The solvent for the physiologically active substance and polylactic acid is not specifically limited so long as it dissolves both. Preferred examples include halogenated hydrocarbons such as methylene chloride, chloroform, and carbon tetrachloride; aromatic hydrocarbons such as toluene and xylene; and mixed solvents thereof.

The non-solvent used for emulsification should preferably be water or silicone oil which is substantially immiscible with the above-mentioned organic solvent and keeps low the solubility of the physiologically active substance. The non-solvent may also be previously incorporated with a water soluble polymer as an emulsion stabilizer, such as polyvinyl alcohol, polyvinyl pyrrolidone, carboxymethyl cellulose, lecithin, and gelatin.

The emulsification is accomplished by applying ultrasonic wave. Prior to the application of ultrasonic wave, the solution and non-solvent may be mixed using a propeller stirrer or turbine stirrer.

After emulsification, the first solvent is distilled away from the resulting o/w emulsion. Thus there are formed microspheres containing the physiologically active substance. Subsequently, they are separated from the non-solvent by filtration or centrifugation. After separation, they are dried, if necessary.

The concentrations of the physiologically active substance and polylactic acid vary depending on the type of the drug and the object for which the microspheres are used. In the case of anticancer drug, the concentration of the drug based on the amount of polylactic acid should be less than 30% (w/w), preferably 5 to 25% (w/w). Their concentration based on the amount of the solvent should be 1 to 25% (w/v), preferably 5 to 20% (w/v).

The treatment with ultrasonic wave can be accomplished at any temperature so long as the drug and solvent are not adversely affected. Usually it is accomplished at room temperature. The output power of ultrasonic wave and the time of treatment should be properly selected so that an emulsion of desired particle size is obtained. Usually the output power is less than 100W and the time is less than several minutes.

The function and effect of the present invention will be explained with reference to microspheres containing aclarubicin (ACR for short).

(A) Sustained release of drug (1) Three kinds of microspheres (1 to 2 μm in average particle diameter) containing 3%, 5%, and 10% of ACR were prepared from polylactic acid having a molecular weight of about 6,100. They were shook in a phosphate buffer solution (pH 7.4) at 37° C. using a constant temperature bath mounted on a shaker. The amount of ACR which had dissolved was determined at predetermined time intervals for 30 days using hight-performance liquid chromatography (with a fluorimetric detector). The results are shown in FIG. 1. It is noted that the microspheres of the invention do not release the drug in large quantities in the initial stage but they release the drug gradually over a long period of time. The amount of release is approximately proportional to the initial content of the drug. Therefore, with the microspheres, it is possible to maintain a desired dosage level if the initial content of the drug is properly selected.

(2) The dissolution with time of ACR from microspheres containing 10% (w/w) ACR hydrochloride was calculated by the same experiment as mentioned above. The results are shown in Table 1.

TABLE 1

| Period (days) for dissolution | 1 | 3 | 5 | 11 | 15 |
|---|---|---|---|---|---|
| Amount of ACR dissolved (%) | 28 | 53 | 74 | 97 | 100 |

The loss of drug that takes place during the preparation of microspheres is negligible; therefore, the microspheres permit the effective use of the drugs.

(3) The effect of the molecular weight of polylactic acid on the dissolution of ACR was investigated by performing the dissolution test (in the same manner as mentioned above) for microspheres prepared in Example 1 mentioned later. The results are shown in Table 2.

TABLE 2

| Test No. | MW of polylactic acid | ACR content, g (10% W/W) | Dissolution (%) after days | | | | | |
|---|---|---|---|---|---|---|---|---|
| | | | 1 | 2 | 5 | 10 | 20 | 30 |
| 1 | ca. 3,600 | 0.2 | 19.3 | 22.6 | 32 | 44 | 61 | 78 |
| 2 | ca. 4,800 | 0.2 | 10 | 12 | 17 | 24 | 41 | 49 |
| 3 | ca. 6,100 | 0.2 | 10.7 | 13 | 22 | 34 | 55 | 63 |
| 4 | ca. 7,200 | 0.2 | 4 | 5 | 7 | 12 | 21 | 32 |

It is noted from Table 2 that with the microspheres of the invention, it is possible to control the rate of sustained release of the drug by changing the molecular weight of the polylactic acid used for the microspheres.

(B) Directionality in living body

Microspheres containing ACR hydrochloride were intraperitoneally administered to rats, and the concentration of ACR in plasma and thoracic duct lymph was determined by the following method.

Microspheres containing 10% (w/w) of ACR were prepared from polylactic acid having an average molecular weight of about 6100 in the same manner as in Section (A) mentioned above. The microspheres in an amount equivalent to a dosage of 1 mg/kg (as ACR) were suspended in 0.5 ml of sterilized physiological saline solution. The suspension was intraperitoneally administered to male Wistar rats (weighing 350 to 400 g). The concentration of ACR in plasma and thoracic duct lymph was determined at predetermined intervals over a period of 13 days. The results are shown in FIG. 2.

Figure 2:
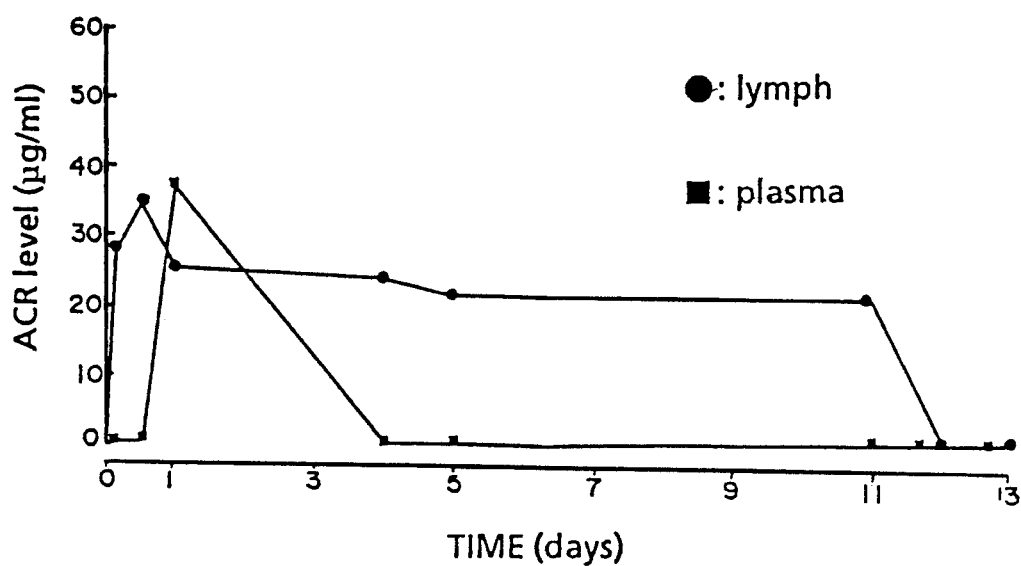
FIG. 2 is a graph showing the change of ACR concentration that takes place in plasma and thoracic duct lymph after intraperitoneal administration of ACR-containing microspheres to rats.

It is noted from FIG. 2 that the concentration of ACR determined one day after administration was 30 to 40 ng/ml in both plasma and thoracic duct lymph. However, the concentration of ACR in plasma gradually decreased with time and no ACR was detected after the fourth day. On the other hand, the concentration of ACR in thoracic duct lymph remained at a level of 20 to 30ng/ml until the eleventh day after administration. These results indicate that the intraperitoneally administered microspheres provide the directionally of ACR toward lymph over a long period of time. Therefore, the microspheres of the invention will find use as a chemotherapeutic means to remedy and prevent lymph metastatic carcinoma.

(C) Effect of ultrasonic wave on particle size

To investigate the effect of ultrasonic wave on particle size, microspheres were prepared by dissolving ACR in a methylene chloride solution of polylactic acid, dispersing the resulting solution into water containing polyvinyl alcohol as a stabilizer, and performing emulsification by the aid of ultrasonic wave under varied conditions. The thus obtained microspheres were observed under a scanning electron microscope. It was confirmed that the microspheres are composed of spherical particles.

In the case where ultrasonic wave was applied at an output of 15W for 30 seconds, the average particle diameter was about 5 μm. The application of ultrasonic wave at an output of 60W for 30 seconds provided microspheres having an average particle diameter of about 1 μm. These results indicate that it is possible to control the particle diameter of the microspheres containing a physiologically active substance if the application of ultrasonic wave is performed under proper conditions.

The invention will be explained in more detail with reference to the following examples.

EXAMPLE 1

Polylactic acid microspheres containing ACR were prepared in the following manner. Two grams of poly-L-lactic acid having a weight-average molecular weight of about 3600 was dissolved in 20 ml of methylene chloride. In the resulting solution was dissolved 0.2 g of ACR. The resulting solution was added dropwise with stirring to 200 ml of a 2% (w/w) aqueous solution of polyvinyl alcohol. The solution was emulsified for about 30 seconds using an ultrasonic emulsifier (transducer: 20 mm in diameter, output: 100 W) made by Nippon Seiki Seisakusho Co., Ltd. The methylene chloride was distilled away from the emulsion by stirring the emulsion at room temperature.

The thus obtained microspheres were observed under an optical microscope. It was found that the particle diameter was smaller than 10 μm and the average particle diameter was about 1 to 2 μm. The dissolution test indicated that almost all ACR was trapped in the microspheres.

EXAMPLES 2 to 4

The same procedure as in Example 1 was repeated except that the poly-L-lactic acid was replaced by one having a weight-average molecular weight of 4800, 6100, and 7200, respectively. The resulting microspheres had an average molecular weight of about 1 to 2 μm, and contained no particles larger than 10 μm.

EXAMPLES 5 to 7

Figure 3:
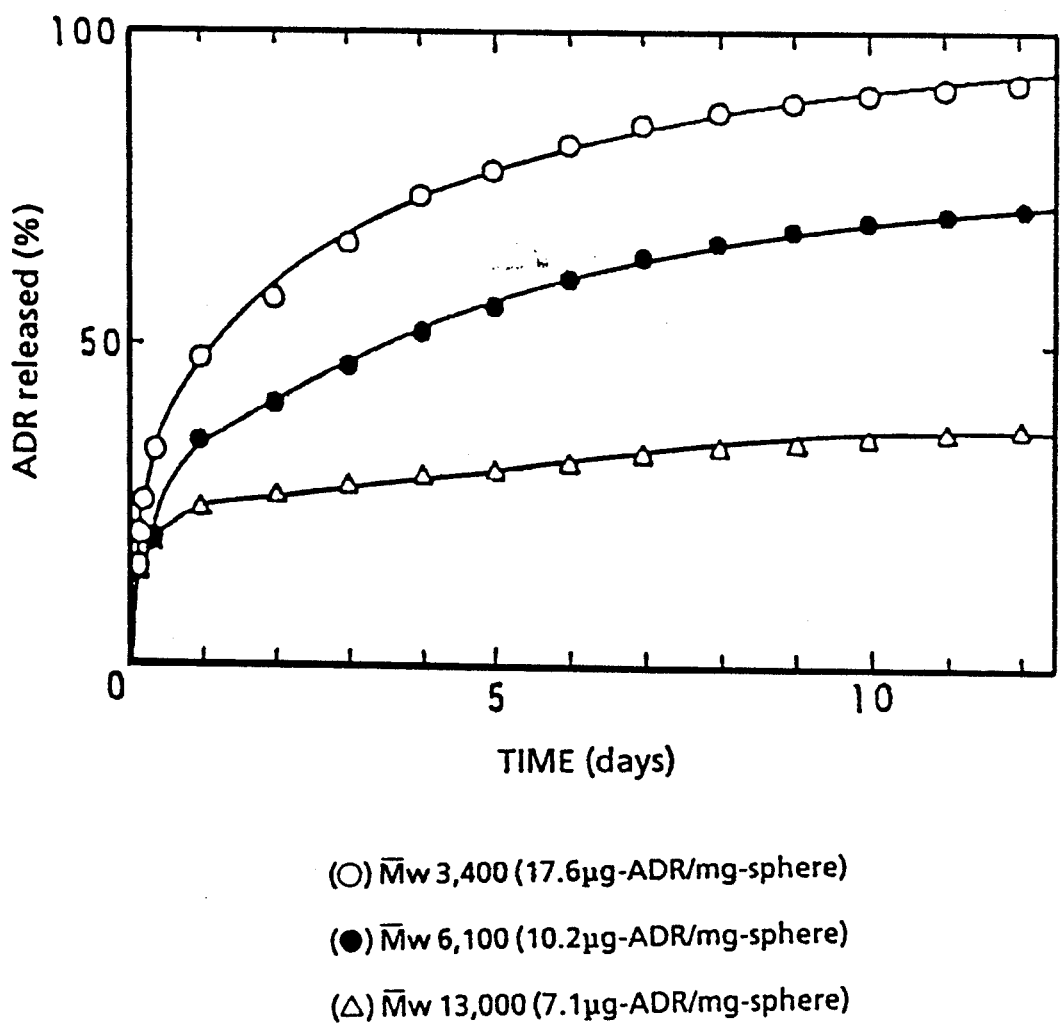
FIG. 3 is a graph showing the release of ADR from polylactic acid microspheres.

The same procedure as in Example 1 was repeated except that the poly-L-lactic acid was replaced by one having a weight-average molecular weight of 3400, 6100, and 13,000, respectively, and the ACR was replaced by 40 mg of adriamycin (ADR for short). The resulting microspheres were composed of fine particles as in Example 1. Incidentally, ADR was trapped in the microspheres at a ratio of about 88.0%, 51.2%, and 36.0%, respectively, in the three examples. The release of ADR from the microspheres is shown in FIG. 3.

EXAMPLE 8

The same procedure as in Example 1 was repeated except that the poly-L-lactic acid was replaced by the one having a weight-average molecular weight of 4700, and the ACR was replaced by 0.2 g of 5-fluorouracil (5-FU for short). The resulting microspheres were composed of fine particles as in Example 1. Incidentally, almost all 5-UF was trapped in the microspheres. The release of 5-UF was similar to that of ACR trapped in the microspheres made of polylactic acid having a molecular weight of 3400.

What is claimed is:

1. A method of enhancing phagocytosis during the controlled sustained release of a physiologically-active substance in a pharmaeutical preparation comprising administering to a host an effective amount of a pharmaceutical preparation comprising spherical microspheres of polylactic acid, said microspheres having entrapped therein said physiologically-active substance, and utilizing said microspheres in a form having an average particle diameter of 1 to 2 μm to enhance phagocytosis as said physiologically-active substance is being released from said microspheres in a sustained manner over time.

2. A method as in claim 1, wherein said physiologically-active substance is an anticancer drug.

3. A method as in claim 2, wherein said pharmaceutical preparation comprises a solution having said microspheres suspended therein, and wherein said pharmaceutical preparation is administered to said host intraperitoneally, whereby said microspheres provide a directionality of said anticancer drug toward lymph in said host.

4. A method as in claim 1, wherein said physiologically-active substance has a concentration of 5 to 25% w/w based on the amount of said polylactic acid.

5. A method as in claim 1, said polylacitic acid having a molecular weight of about 3000 to 7500.

* * * * *